United States Patent
Sharma et al.

(10) Patent No.: US 6,541,193 B2
(45) Date of Patent: *Apr. 1, 2003

(54) SCREENING THE ACTIVITY OF DRUGS FOR CENTRAL NERVOUS SYSTEM (CNS)

(75) Inventors: Abhay Sharma, Lucknow (IN); Sushil Kumar, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 7 days.

This patent is subject to a terminal disclaimer.

(21) Appl. No.: 09/789,525

(22) Filed: Feb. 22, 2001

(65) Prior Publication Data

US 2002/0115129 A1 Aug. 22, 2002

(51) Int. Cl.$^7$ .......................... C12Q 1/00; G01N 33/00; A01K 67/033; C12N 15/00
(52) U.S. Cl. .................. 435/4; 800/3; 800/13; 800/22
(58) Field of Search .......................... 435/4; 800/3, 13, 800/22

(56) References Cited

U.S. PATENT DOCUMENTS 6,291,739 B1 * 3/2000 Sharma et al.

* cited by examiner

Primary Examiner—Jon P. Weber
Assistant Examiner—Kailash C. Srivastava
(74) Attorney, Agent, or Firm—Foley & Lardner

(57) ABSTRACT

The invention relates to a method for screening of neuroactive drugs using the fruit fly *Drosophila melanogaster*, which comprises the steps of, generating a double mutant line of K$^+$ channel genes in *Drosophila melanogaster*; culturing the Sh$^5$eag$^1$ mutant flies on Dorsophila medium under standard conditions; and anesthetizing flies with diethyl ether and observing the time taken by flies to recover from anesthesia.

6 Claims, No Drawings

SCREENING THE ACTIVITY OF DRUGS FOR CENTRAL NERVOUS SYSTEM (CNS)

FIELD OF THE INVENTION

This invention relates to the development of a novel test model and assay for screening the activity of drugs for central nervous system (CNS). More particularly, the invention identifies the use of the fruit fly as a model to test the neuroactivity of test drugs/samples.

BACKGROUND OF THE INVENTION

Drugs that stimulate or depress CNS play an important role in human therapeutics. They act as anesthetics, analgesics, sedatives, psychostimulants, analeptics, antidepressants, anticonvulsants etc. and are used in the treatment of conditions such as narcolepsy, depression, hyperactivity disorders, epilepsy and drug addiction in human (Wood-Smith and Stewart, 1964, in Drugs in anesthetic practice, Butterworth; Beckman, 1958, in Drugs, their nature, action and use, W. B. Saunder, Green and Levy, 1976, Drug misuse, human abuse, Dekker). Undesirable side effects and ineffectiveness of currently available CNS stimulants/depressants in many situations call for development of novel drugs.

Animal models currently used in neuroactive drug screening mostly include higher animals such as nonhuman primates and rodents. Although their indispensability in advanced stages of drug development can not be denied, using these models in primary rug screening is time, cost and labor intensive. Many components of neuronal signaling are conserved between the fruit fly Drosophila melanogaster and human (Rubin e al, 2000, Science 287:2204–2215; Littleton and Ganetzky, 2000, Neuron 26:35–43). Moreover, many CNS stimulant/depressant drugs used in human therapy also exhibit their neuroactivity in fly (Shaw et al, 2000, Science 287:1834–1837; Hendricks et al, 2000, Neuron 25:129–138; Andretic et al, 1999, Science 285:1066–1068; Li et al, 2000, Curr. Biol. 10:211–214; Baintaon et al, 2000, Curr. Biol. 10:187–194; McClung and Hirsh, 1999, Curr. Biol. 9:853–860). Considering these, the applicants thought of evaluating of potential of Drosophila to serve as a simple, rapid and inexpensive model for screening of CNS active agents.

A variety of CNS stimulant/depressant drugs have originated from plants (Wood-Smith and Stewart, 1964, in Drugs in anesthetic practice, Butterworth; Beckman, 1958, in Drugs, their nature, action and use, W. B. Saunder; Green and Levy, 1976, Drug misuse, human abuse, Dekker, Plotkin, 2000, in Medicine quist in search of nature's healing secrets, Viking; Gratzer, 2000, Nature 406:235–236). There are several reasons why neuroactive compounds made by plants work on receptors in human brain is also (Lam et al, 1998, Nature 396:125–126). Keeping the above in view, the applicant used the fly model plant samples and developed a simple assay for screening of substances and evaluate their utility in drug screening.

OBJECTS OF THE INVENTION

The main object of the invention is to provide a novel method for screening of neuroactive drugs using the fruit fly Drosophila melanogaster as an in vivo model.

Another object is to develop a method for simultaneous screening of antiepileptic and central nervous system stimulant/depressant classes of drugs.

Yet another object is to provide a simple and cost-effective method for studying the neuroactivity of a substance using Drosophila melanogaster as a model.

SUMMARY OF THE INVENTION

Accordingly, the invention provides a novel method for screening of neuroactive drugs using Drosophila melanogaster as an in vivo test model. The invention also provides methods for studying the neuroactivity of a substance using Drosophila melanogaster as a model.

DETAILED DESCRIPTION

The invention relates to a method for screening of neuroactive drugs using the fruit fly Drosophila melanogaster, which comprises the steps of:

a) generating a double mutant line of $K^+$ channel genes in Drosophila melanogaster;

b) culturing the $Sh^5 eag^1$ mutant flies on Dorsophila medium under standard conditions; and c) anesthetizing flies with diethyl ether and observing the time taken by flies to recover from anesthesia.

In an embodiment, decreased arousal time in flies treated with normal fly food mixed with the agent being screened, compared to flies fed on normal fly food, is indicative of analeptic activity of the agent.

In another embodiment, an early arousal in flies treated with normal fly food mixed with both the agent being screened as well as the drug phenobarbital, compared to flies fed on normal fly food mixed with phenobarbital alone, is indicative of an analeptic activity of the agent.

In yet another embodiment, spontaneous locomotor activity is observed.

In still another embodiment, increased locomotor activity in flies treated with normal fly food mixed with both the agent being screened as well as ethanol, compared to flies fed on normal fly food mixed with ethanol alone, is indicative of an analeptic activity of the agent.

In an embodiment, an increased locomotor activity in flies treated with normal fly food mixed with the agent being screened, compared to flies fed on normal fly food, is indicative of a psychostimulant activity of the agent.

Thus, the present invention relates to a novel method for screening of CNS active agents. Ether-sensitive leg shaking phenotype of Drosophila melanogaster $K^+$ channel double mutant $Sh^5 eag^1$ has been earlier evaluated by the applicants as a target for antiepileptic drug screening (Sharma and Kumar, 2000, U.S. patent application Ser. No. 09/535,517). To further enhance the usefulness of $Sh^5 eag^1$ in neuroactive drug screening the applicants studied the effect of a CNS depressant drug, phenobarbital, on time taken by flies to recover from ether anesthesia. The drug was found to delay recovery. This suggested that a change in recovery time could be exploited as a screening criterion for CNS active drugs. A comparison between $Sh^5 eag^1$ and Oregon-R wild-type flies revealed that recovery is faster in the former. This indicated the advantage of mutant over wild-type in speeding up the process of drug screening. The position of $Sh^5 eag^1$ as an efficient neuroactive drug testing model was therefore further consolidated. The model thus evolved was applied for screening of the targeted activities in plant extracts. Out of 50 plant species screened, one was found to test positive. Further experiments confirmed that the plant substance screened has analeptic and psychostimulant properties (Sharma et al, a substance from Acorus calamus plant with analeptic and psychostimulant properties, a separate patent filed). This demonstrates the practical usefulness of the fly model developed. Accordingly, the present invention provides a CNS drug screening method, which comprises use of the fruit fly *Drosophila melanogaster* as a whole organism in vivo model for drug testing.

Vertebrate animal models currently used for screening of neuroactive agents are time, labor and cost intensive. The applicants therefore thought of using fruit fly *Drosophila melanogaster* as a simple, rapid and inexpensive in vivo whole organism behavioral model for primary drug screening. In this context, we previously validated the ether-sensitive leg shaking phenotype in $K^+$ channel double mutant $Sh^5eag^1$ as a target for antiepileptic drug screening (Sharma and Kumar, 2000, U.S. patent application Ser. No. 09/535,517). To add value to this model, it was desirous to exploit it for simultaneous screening of other CNS active drugs. Anesthetics produce a profound depression of CNS and, therefore, we wondered if recovery from anesthesia in flies could serve as a simple means to rapidly screen CNS depressants/stimulants. To explore this possibility, the applicants studied the effect of known CNS depressant, phenobarbital, on time taken by $Sh^5eag^1$ flies to recover from ether anesthesia. It turned out that the drug delays recovery. A change in recovery time was therefore validated as a criterion for screening CNS active agents. While applying $Sh^5eag^1$ in antiepileptic drug screening, the applicants noticed that the mutant flies recover from ether anesthesia earlier than wild-type ones. If it is so, we thought, then the time required to test a sample in the mutant would be less than that in the wild-type and, therefore, screening in $Sh^5eag^1$ would be much faster. To verify the difference in recovery time, we compared the performance of $Sh^5eag^1$ and the wild-type Oregon-R after ether anesthesia. A quick recovery in the mutant was confirmed. The above mentioned results therefore led to the development of $Sh^5eag^1$ as a model for screening CNS depressants/stimulants. This added to the usefulness of the mutant in drug screening because it is already serving as a screen for antiepileptic drugs. The use of Drosophila $Sh^5eag^1$ as a test model is novel of illustrated by the following examples, which should not be construed to limit the scope of the invention in any manner.

EXAMPLE 1

Standard Drosophila manipulation methods were followed. Cultures were grown on a medium containing maize powder, sugar, yeast and Nipagin. Flies were maintained and further manipulated at room temperature. Experimental conditions were kept identical. The double mutant $Sh^5eag^1$ was generated using standard methods of Drosophila genetics.

Equal number of $Sh^5eag^1$ males, varying in age between 6–9 days, were treated in 25×100 mm glass vials with either normal food (NF) or food containing 1 mg/ml of phenobarbital sodium (PS; NF+PS) for 5 days. Twenty males were treated in each vial. Flies were first anesthesized with ether and healthy looking individuals shifted to 10 empty vials in such a way that each vial received two flies, one from each treatment. Before shifting, flies from one of the two treatments were marked on their wings for the purpose of identification. Flies were allowed to recover fully. After an hour, each fly pair was subjected to the following test one by one. The two flies, inside a vial with 800 mg of cotton plug, were simultaneously anesthetized by pouring 0.2 ml of diethyl ether on to the plug. After about 1.5 min, during which the vial was gently shaken continuously so that the flies remained at the bottom throughout, the two individuals were immediately shifted to two fresh empty vials. Time at this point was considered 0 min. Etherisation caused the flies to become completely immobile and be on their back. Care was taken to leave the flies in similar position in both the vials. Flies were now constantly watched very carefully. As soon as a fly first time stood up on its legs, time past 0 min was recovered in min, after rounding off. This time was considered to represent recovery time. NF and NF+PS flies were found to recover in 2.4±0.44 and 7.2±1.78 min respectively. The difference (p<0.02) observed between drug treated and untreated flies established that PS delays recovery from ether anesthesia. This result suggested that the time taken by flies to recover from ether anesthesia could be exploited as a drug screening target.

EXAMPLE 2

Recovery time in NF treated $Sh^5eag^1$ mutant and Oregon-R wild-type flies was also determined using the above method, except that 8 instead of 10 pairs were examined and it was found to be 6.25±1.30 and 24.12±2.11 min respectively. The difference (p<0.001) observed demonstrated a faster recovery following ether anesthesia in the mutant flies. This result suggested that drug screening using $Sh^5eag^1$ would be much faster than that using Oregon-R.

EXAMPLE 3

Around 200 plant extracts, representing different part of more than 20 plant species, were prepared using hexane, chloroform, acetone, methanol and ethanol as extraction medium. The plant part were dried, ground and soaked sequentially in various solvents, in the order given above, at room temperature. The plant materials were soaked in a particular solvent for 3 days, each day the treated solvent being recovered and replaced with fresh solvent. The three batches of the treated solvents were then pooled together. The extracts were finally obtained by steam distillation followed by evaporation at 37° C. of the remaining solvent. The samples were uniquely coded and stored at 10° C. till further use.

A blind screening of coded plant extracts was performed in the following manner. Extracts were dissolved in ethanol at a concentration of 40–50 mg/ml. Either freshly prepared alcoholic samples or ethanol alone were thoroughly mixed, 5% (v/v), in melted fly medium mentioned earlier. The media so prepared was poured in 25×100 mm glass vials, 2–3 ml each. The media was allowed to solidify at room temperature, before being kept at 10° C. overnight. Vials were brought to room temperature and then 15–20 $Sh^5eag^1$ male flies were shifted to each vial. Fly culture conditions and fly manipulation methods used were as described earlier. At least two replicates were set up for each of the two treatments, namely, normal food (NF) and normal food with extract (NF+EX). The vials containing flies were kept in an inverted position, with medium at the top and cotton plug at the bottom, for 5–6 days at room temperature. Two groups, one from NF and the other from NF+EX treatment, of 10–12 flies each were etherized and then allowed to recover in parallel in two vials under exactly identical conditions. Flies were observed to see if NF+EX treated ones tend to recover earlier or later than those treated with NF. Two replicates were similarly examined.

The above screening resulted in the detection of two extracts that delayed recovery from ether anesthesia in flies (Sharma et al, a substance from *Acorus calamus* plant with analeptic and psychostimulant properties, a separate patent filed). Further experiments with one of the extract showed a similar activity in flies anesthetized by chloroform. In addition, the extract was also found to suppress delay in recovery from their anesthesia caused by phenobarbital and to suppress decrease in spontaneous locomotor activity caused by ethanol in flies. Further, the extract enhanced the spontaneous locomotor activity in normal flies not under drug's influence. These activities of the substance screened show that it has analeptic and psychostimulant properties (Sharma et al, a substance from *Acorus calamus* plant with analeptic and psychostimulant properties). The above screening result therefore demonstrates the practical usefulness of the fly model developed.

Advantages of the Invention

1. Neuroactive drug screening in fly model described here is simple, rapid and inexpensive, compared to that in currently used animal models such as rat, mouse etc.

2. The present fly model can be used for dual screening, i.e., simultaneous screening of both antiepileptic and CNS stimulant/depressant classes of drugs.

3. Drosophila is already a well established experimental organism. Its use described here further demonstrates its worth in drug screening.

4. Since the fruit fly is amenable to genetic and molecular analysis, the neuroactivity of substance screened using the present model can be further studied directly in this organism.

5. The CNS active substance screened using this fly model can serve as a tool in studies pertaining to anesthesia. This is all the more important considering the status of Drosophila as an anesthesia model.

6. Unlike conventional drug screening animal models, fly model does not antagonize animal rights' ethics.

What is claimed is:

1. A method for identifying a substance that has analeptic activity on the central nervous system, comprising (a) feeding for at least 5 days (i) a first *Drosophila melanogaster* mutant fly, $Sh^5eag^1$, with normal food, and (ii) a second $Sh^5eag^1$ mutant fly with normal food containing a test substance; (b) anesthetizing said first and second $Sh^5eag^1$ mutant flies with diethyl ether; and (c) observing the time taken by said first and second $Sh^5eag^1$ mutant flies to recover from said diethyl ether anesthesia, wherein a shorter time of recovery in said second $Sh^5eag^1$ mutant fly compared to said first $Sh^5eag^1$ mutant fly indicates that said test substance is a substance that has analeptic activity.

2. The method of claim 1, further comprising admixing phenobarbital to both (i) the normal food and to (ii) the normal food containing a test substance, prior to step (a), wherein a shorter time of recovery in said second $Sh^5eag^1$ mutant fly compared to said first $Sh^5eag^1$ mutant fly indicates that said test substance is a substance that has analeptic activity.

3. The method of claim 1, wherein spontaneous locomotor activity is indicative of the time taken by said first and second $Sh^5eag^1$ mutant flies to recover from said diethyl ether anesthesia in step (c).

4. The method of claim 3, wherein an increase in spontaneous locomotor activity in said second $Sh^5eag^1$ mutant fly compared to said first $Sh^5eag^1$ mutant fly indicates that said test substance is a substance that is a pyschostimulant.

5. The method of claim 1, further comprising admixing ethanol to both (i) the normal food and to (ii) the normal food containing a test substance, prior to step (a), wherein increased locomotor activity in said second $Sh^5eag^1$ mutant fly compared to said first $Sh^5eag^1$ mutant fly indicates that said test substance is a substance that has analeptic activity.

6. The method of claim 1, wherein the step of anesthetizing said first and second $Sh^5eag^1$ mutant flies with diethyl ether comprises pouring 0.2 ml of diethyl ether on to a cotton plug affixed upon vials in which said mutant flies are contained.

* * * * *